United States Patent
Kim (10) Patent No.: US 12,004,626 B2
(45) Date of Patent: Jun. 11, 2024

(54) FOOT EXFOLIATOR WITH HIGH-GLOSS NAIL POLISHER, AND ELECTRIC FOOT EXFOLIATION KIT

(71) Applicant: Chulha Kim, Icheon-si (KR)

(72) Inventor: Chulha Kim, Icheon-si (KR)

( * ) Notice: Subject to any disclaimer, the term of this patent is extended or adjusted under 35 U.S.C. 154(b) by 156 days.

(21) Appl. No.: 17/565,623

(22) Filed: Dec. 30, 2021

(65) Prior Publication Data
US 2023/0009505 A1  Jan. 12, 2023

(30) Foreign Application Priority Data

Jul. 12, 2021  (KR) ........................ 10-2021-0090921

(51) Int. Cl.
*A45D 29/12*  (2006.01)
*A45D 29/11*  (2006.01)
(Continued)

(52) U.S. Cl.
CPC .............. *A45D 29/12* (2013.01); *A45D 29/11* (2013.01); *A45D 29/18* (2013.01); *A61B 17/54* (2013.01)

(58) Field of Classification Search
CPC ...... A45D 29/04; A45D 29/045; A45D 29/05; A45D 29/06; A45D 29/11; A45D 29/12; A45D 29/14; A45D 29/17; A45D 29/18; A45D 29/00; A45D 2029/045; A61B 17/54; A61B 2017/00761; A61B 2017/00747; B24D 15/02; B24D 15/04
(Continued)

(56) References Cited

U.S. PATENT DOCUMENTS

2002/0045907 A1*  4/2002  Sherman .............. A61B 17/205
                                                           606/131
2005/0066988 A1*  3/2005  Park ...................... A61B 17/54
                                                           132/76.4
(Continued)

FOREIGN PATENT DOCUMENTS

AU     7905398 A   *  2/1999
EP     3659464 A1  *  6/2020  ............. A47K 7/026
(Continued)

OTHER PUBLICATIONS

Clarivate Analytics copywritten translation of KR20200067432A; Jun. 12, 2020 (Year: 2020).*
(Continued)

*Primary Examiner* — Jacqueline T Johanas
*Assistant Examiner* — Sarah Woodhouse
(74) *Attorney, Agent, or Firm* — Bridgeway IP Law Group, PLLC; Sang Ho Lee; Hyun Woo Shin (57) ABSTRACT

Provided is a foot exfoliator with a high-gloss nail polisher in which one surface of a hard plate such as a glass plate is divided into a foot exfoliating region and a nail polishing region, the foot exfoliator including a foot exfoliating part, in which one protrusion selected from protrusions having a circular shape, an elliptical shape, and a rhombic shape and a protrusion column are periodically and repeatedly arranged in a predetermined region of the plate, and a nail polishing part, in which a plurality of vertical stripe protrusions or inclined stripe protrusions are arranged to perform nail polishing in regions of an area of the plate excluding the foot exfoliating part.

4 Claims, 4 Drawing Sheets

(51) Int. Cl.
*A45D 29/18* (2006.01)
*A61B 17/54* (2006.01)

(58) Field of Classification Search
USPC .................. 451/523, 524, 530; 132/76.4
See application file for complete search history.

(56) References Cited

U.S. PATENT DOCUMENTS

| | | | | |
|---|---|---|---|---|
| 2008/0230081 | A1* | 9/2008 | Moon | A61B 17/54 |
| | | | | 132/75.6 |
| 2015/0201969 | A1* | 7/2015 | Dugo | A61B 17/54 |
| | | | | 606/131 |

FOREIGN PATENT DOCUMENTS

| | | | |
|---|---|---|---|
| KR | 100723456 B1 * | 5/2007 | |
| KR | 20100103264 A * | 9/2010 | |
| KR | 10-2018-0023666 A | 3/2018 | |
| KR | 10-2021-0051821 A | 5/2021 | |

OTHER PUBLICATIONS

Clarivate Analytics copywritten translation of CZ34648U1; Dec. 8, 2020 (Year: 2020).*
Clarivate Analytics copywritten translation of KR20180023666A; Mar. 7, 2018 (Year: 2018).*
Clarivate Analytics copywritten translation of cn215076098U; Dec. 10, 2021 (Year: 2021).*
Clarivate Analytics copywritten translation of FR3080752A2; Nov. 8, 2019 (Year: 2019).*
Clarivate Analytics copywritten translation of JP2019025310A; Feb. 21, 2019 (Year: 2019).*
Clarivate Analytics copywritten translation of JP59201765A; Nov. 15, 1984 (Year: 1984).*
Clarivate Analytics copywritten translation of KR100846444b1; Jul. 16, 2008 (Year: 2008).*
Clarivate Analytics copywritten translation of KR101672525b1; Nov. 3, 2016 (Year: 2016).*
Clarivate Analytics copywritten translation of KR101773432B1; Aug. 31, 2017 (Year: 2017).*
Clarivate Analytics copywritten translation of KR101900941B1; Sep. 21, 2018 (Year: 2018).*
Clarivate Analytics copywritten translation of KR101901315B1; Sep. 21, 2018 (Year: 2018).*
Clarivate Analytics copywritten translation of KR101914210B1; Feb. 11, 2018 (Year: 2018).*
Clarivate Analytics copywritten translation of KR102028619B1; Nov. 4, 2019 (Year: 2019).*
Clarivate Analytics copywritten translation of KR102157112B1; Sep. 17, 2020 (Year: 2020).*
Clarivate Analytics copywritten translation of KR200319276Y1; Jul. 7, 2003 (Year: 2003).*
Clarivate Analytics copywritten translation of KR200336540Y1; Dec. 18, 2003 (Year: 2003).*
Clarivate Analytics copywritten translation of KR200492337Y1; Sep. 18, 2020 (Year: 2020).*
Clarivate Analytics copywritten translation of KR20160111812A; Sep. 27, 2016 (Year: 2016).*

* cited by examiner

FOOT EXFOLIATOR WITH HIGH-GLOSS NAIL POLISHER, AND ELECTRIC FOOT EXFOLIATION KIT

CROSS-REFERENCE TO RELATED APPLICATION

This application claims priority to and the benefit of Korean Patent Application No. 10-2021-0090921, filed on Jul. 12, 2021, the disclosure of which is incorporated herein by reference in its entirety.

BACKGROUND

1. Field of the Invention

The present invention relates to a foot exfoliator with a high-gloss nail polisher and an electric foot exfoliation kit, and more particularly, to a foot exfoliator with a high-gloss nail polisher and an electric foot exfoliation kit coupled to the foot exfoliator that are nail and foot care tools made of a hard material such as glass and that remove dead skin cells without damaging the living skin so as to make soles of feet smooth.

2. Discussion of Related Art

In general, nail polishers and foot exfoliators have certain patterns formed at certain intervals on a glass surface to polish the nails and skin to remove dead skin cells therefrom and make them glossy or have protrusions formed in a hexagonal honeycomb shape to trim the nails.

The nail polisher and foot exfoliator are made as follows. Chromium (Cr) and metal with excellent chemical resistance are formed on a hard substrate such as a glass substrate, a photosensitive film such as a photoresist (PR) film or a dry film photoresist (DFR) film is coated thereon to form a protrusion pattern on the glass, a mask having a protrusion pattern is placed on the PR (or DFR) film to form protruding portions of the nail polisher, the mask is exposed to ultraviolet (UV) light so that protrusion images are photosensitized on the photosensitive film, the glass substrate irradiated with UV light is immersed in a developer so that the protrusion pattern is formed on the PR (or DFR) film, and then Cr and glass formed under the PR are sequentially etched so that protrusions are formed on the glass.

The hexagonal arrangement of protrusions has a problem in that, when polishing is performed in horizontal and vertical directions, since intervals between non-protruding portions are large, scratching may occur on the nail and thus the nail may not become glossy, or serious damage may be caused to the skin when removing dead skin cells from a sole of a foot.

The applicant of the present invention has filed an application for the invention "High-gloss nail polisher and foot exfoliator making feet smooth (Application No. 10-2019-0137581)" in 2019. The invention has advantages in nail care due to circular, elliptical, and rhombic protrusions being arranged to overlap each other but does not have an effect of completely addressing the above-mentioned problems.

To address the above-mentioned problems, the present invention is directed to providing a foot exfoliator with a high-gloss nail polisher in which a foot exfoliating part and a nail polishing part are configured together, wherein, in the foot exfoliating part, one or more protrusions, among circular, elliptical, and rhombic protrusions, and protrusion columns are arranged at certain intervals to safely remove the hard dead skin cells formed on a heel of a sole without causing skin damage, and in the nail polishing part, stripe protrusions are arranged to make nails, which are part of the human body, glossy.

As another embodiment, the present invention is directed to providing an electric rotary polishing foot exfoliation kit for a foot exfoliator that is capable of being coupled to the foot exfoliator to easily remove dead skin cells.

SUMMARY OF THE INVENTION

The present invention is directed to providing a foot exfoliator with a high-gloss nail polisher in which one surface of a hard plate such as a glass plate is divided into a foot exfoliating part and a nail polishing part.

The present invention is also directed to providing a foot exfoliator with a high-gloss nail polisher in which, in the foot exfoliating part, one protrusion selected from circular, elliptical, and rhombic protrusions and a protrusion column are periodically and repeatedly arranged in a predetermined area of the plate.

The present invention is also directed to providing a foot exfoliator with a high-gloss nail polisher in which the protrusion column of the foot exfoliating part consists of comb-pattern stripe protrusions or vertical stripe protrusions.

The present invention is also directed to providing a foot exfoliator with a high-gloss nail polisher in which, in the foot exfoliating part to which the comb-pattern stripe protrusions are coupled, a plurality of protrusion regions each formed of one or more protrusions among circular, elliptical, and rhombic protrusions and a plurality of protrusion columns consisting of comb-pattern stripe protrusions formed as if dividing the protrusion regions are arranged on a certain area of the plate.

The present invention is also directed to providing a foot exfoliator with a high-gloss nail polisher in which, between the comb-pattern stripe protrusions of the protrusion columns, any one protrusion selected from circular, elliptical, and rhombic protrusions is further arranged as a plurality of protrusions, or only the comb-pattern stripe protrusions constitute the region.

The present invention is also directed to providing a foot exfoliator with a high-gloss nail polisher in which, in the foot exfoliating part to which the vertical stripe protrusions of the protrusion column are coupled, a plurality of protrusion regions each formed of one or more protrusions among circular, elliptical, and rhombic protrusions and a plurality of protrusion columns consisting of vertical stripe protrusions formed as if dividing the protrusion regions are arranged on a certain area of the plate.

The present invention is also directed to providing a foot exfoliator with a high-gloss nail polisher in which the nail polishing part is divided into a dense region and a loose region, and the stripe protrusions are arranged at different intervals for each region.

The present invention is directed to providing an electric foot exfoliation kit configured on a round surface of a hard circular plate such as a glass plate so as to be coupled to a foot exfoliator to remove dead skin cells.

The present invention is also directed to providing an electric foot exfoliation kit in which one or more protrusions selected from circular, elliptical, and rhombic protrusions and protrusion columns are radially arranged from the center.

The present invention is also directed to providing an electric foot exfoliation kit in which the protrusion column consists of comb-pattern stripe protrusions or vertical stripe protrusions.

The present invention is also directed to providing an electric foot exfoliation kit in which, between the comb-pattern stripe protrusions of the protrusion columns, any one protrusion selected from the circular, elliptical, and rhombic protrusions is further arranged as a plurality of protrusions.

To achieve the above objectives, the present invention provides a foot exfoliator with a high-gloss nail polisher in which one surface of a hard plate such as a glass plate is divided into a foot exfoliating part and a nail polishing part.

In the foot exfoliating part, one protrusion selected from circular, elliptical, and rhombic protrusions and a protrusion column may be periodically and repeatedly arranged in a predetermined area of the plate.

The protrusion column of the foot exfoliating part may consist of comb-pattern stripe protrusions or vertical stripe protrusions.

In the foot exfoliating part to which the comb-pattern stripe protrusions of the protrusion column are coupled, a plurality of protrusion regions each formed of one or more protrusions among circular, elliptical, and rhombic protrusions and a plurality of protrusion columns consisting of comb-pattern stripe protrusions formed as if dividing the protrusion regions may be arranged on a certain area of the plate.

Between the comb-pattern stripe protrusions of the protrusion columns, any one protrusion selected from circular, elliptical, and rhombic protrusions may be further arranged as a plurality of protrusions, or only the comb-pattern stripe protrusions may constitute the region.

In the foot exfoliating part to which the vertical stripe protrusions of the protrusion column are coupled, a plurality of protrusion regions each formed of one or more protrusions among circular, elliptical, and rhombic protrusions and a plurality of protrusion columns consisting of vertical stripe protrusions formed as if dividing the protrusion regions may be arranged on a certain area of the plate.

The nail polishing part may be divided into a dense region and a loose region, and the stripe protrusions may be arranged at different intervals for each region.

The present invention provides an electric foot exfoliation kit which is configured on a round surface of a hard circular plate such as a glass plate.

One or more protrusions selected from circular, elliptical, and rhombic protrusions and protrusion columns consisting of stripe protrusions may be radially arranged from the center.

The stripe protrusions of the protrusion column may be comb-pattern stripe protrusions or vertical stripe protrusions.

Between the comb-pattern stripe protrusions of the protrusion columns, any one protrusion selected from the circular, elliptical, and rhombic protrusions may be further arranged as a plurality of protrusions.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Since various modifications may be made to the present invention and the present invention may have various embodiments, specific embodiments illustrated in the drawings will be described in detail herein.

However, this does not limit the present invention to the specific embodiments, and all modifications, equivalents, and substitutes included in the spirit and scope of the present invention should be construed as belonging to the present invention.

Terms or words used herein are only used to describe specific embodiments and are not intended to limit the present invention. The terms or words used herein should be interpreted as having meanings and concepts which correspond with the technical spirit of the present invention based on the principle that the inventor can properly define the concept of the terms to describe his or her own invention in the best possible way.

Generally, nail polishers and foot exfoliators have certain patterns formed at certain intervals on a glass surface to polish the nails and skin to remove dead skin cells therefrom and make them glossy or have protrusions formed in a hexagonal honeycomb shape to trim the nails.

The hexagonal arrangement of protrusions has a problem in that, when polishing is performed in horizontal and vertical directions, since intervals between non-protruding portions are large, scratching may occur on the nail and thus the nail may not become glossy, or serious damage may be caused to the skin when removing dead skin cells from a sole of a foot.

The applicant of the present invention has filed an application for the invention "High-gloss nail polisher and foot exfoliator making feet smooth (Application No. 10-2019-0137581)" in 2019. The invention has advantages in nail care due to circular, elliptical, and rhombic protrusions being arranged to overlap each other but does not have an effect of completely addressing the above-mentioned problems.

To address the above-mentioned problems, the present invention is directed to providing a foot exfoliator with a high-gloss nail polisher in which a foot exfoliating part and a nail polishing part are configured together, wherein, in the foot exfoliating part, one or more protrusions, among circular, elliptical, and rhombic protrusions, and protrusion columns are arranged at certain intervals to safely remove the hard dead skin cells formed on a heel of a sole without causing skin damage, and in the nail polishing part, stripe protrusions are arranged to make nails, which are part of the human body, glossy.

The present invention is also directed to providing an electric foot exfoliation kit for a foot exfoliator, the electric foot exfoliation kit having protrusions radially formed from the center on a round surface of a circular plate.

Specific features of the present invention and advantages thereof will become more apparent from the following description with reference to the accompanying drawings.

Figure 1:
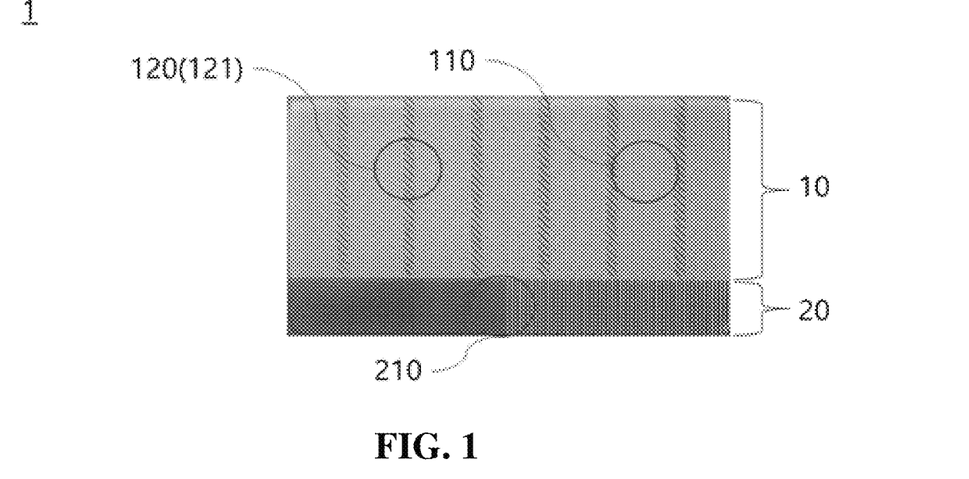
FIG. 1 is a picture showing an embodiment of a foot exfoliator with a high-gloss nail polisher according to the present invention.
Figure 2:
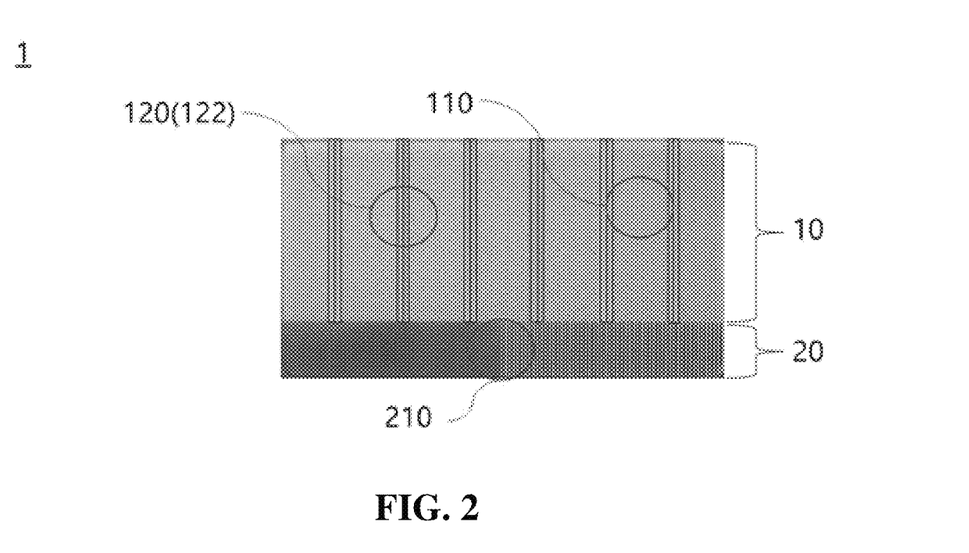
FIG. 2 is a picture showing another embodiment of a foot exfoliator with a high-gloss nail polisher according to the present invention.
Figure 3:
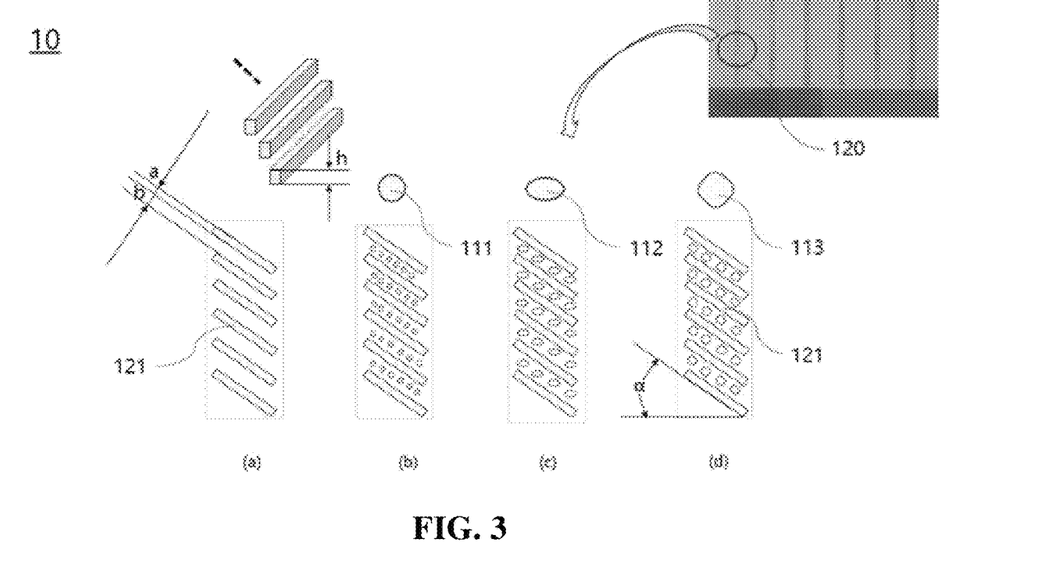
FIG. 3 shows various embodiments of a protrusion column of a foot exfoliating part of the foot exfoliator with the high-gloss nail polisher according to the present invention, wherein FIG. 3A schematically shows an embodiment in which only comb-pattern stripe protrusions are arranged, FIG. 3B schematically shows an embodiment in which circular protrusions are arranged between the comb-pattern stripe protrusions, FIG. 3C schematically shows an embodiment in which elliptical protrusions are arranged between the comb-pattern stripe protrusions, and FIG. 3D schematically shows an embodiment in which rhombic protrusions are arranged between the comb-pattern stripe protrusions.
Figure 4:
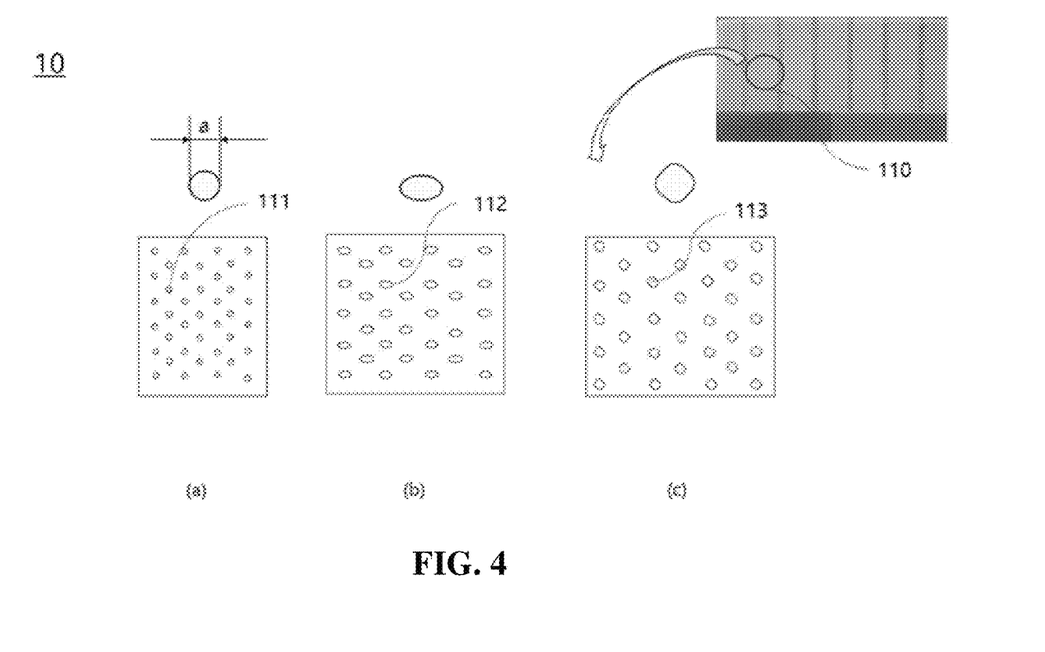
FIG. 4 shows various embodiments of a protrusion region of the foot exfoliating part of the foot exfoliator with the high-gloss nail polisher according to the present invention, wherein FIG. 4A schematically shows an embodiment in which circular protrusions are arranged, FIG. 4B schematically shows an embodiment in which elliptical protrusions are arranged, and FIG. 4C schematically shows an embodiment in which rhombic protrusions are arranged.
Figure 5:
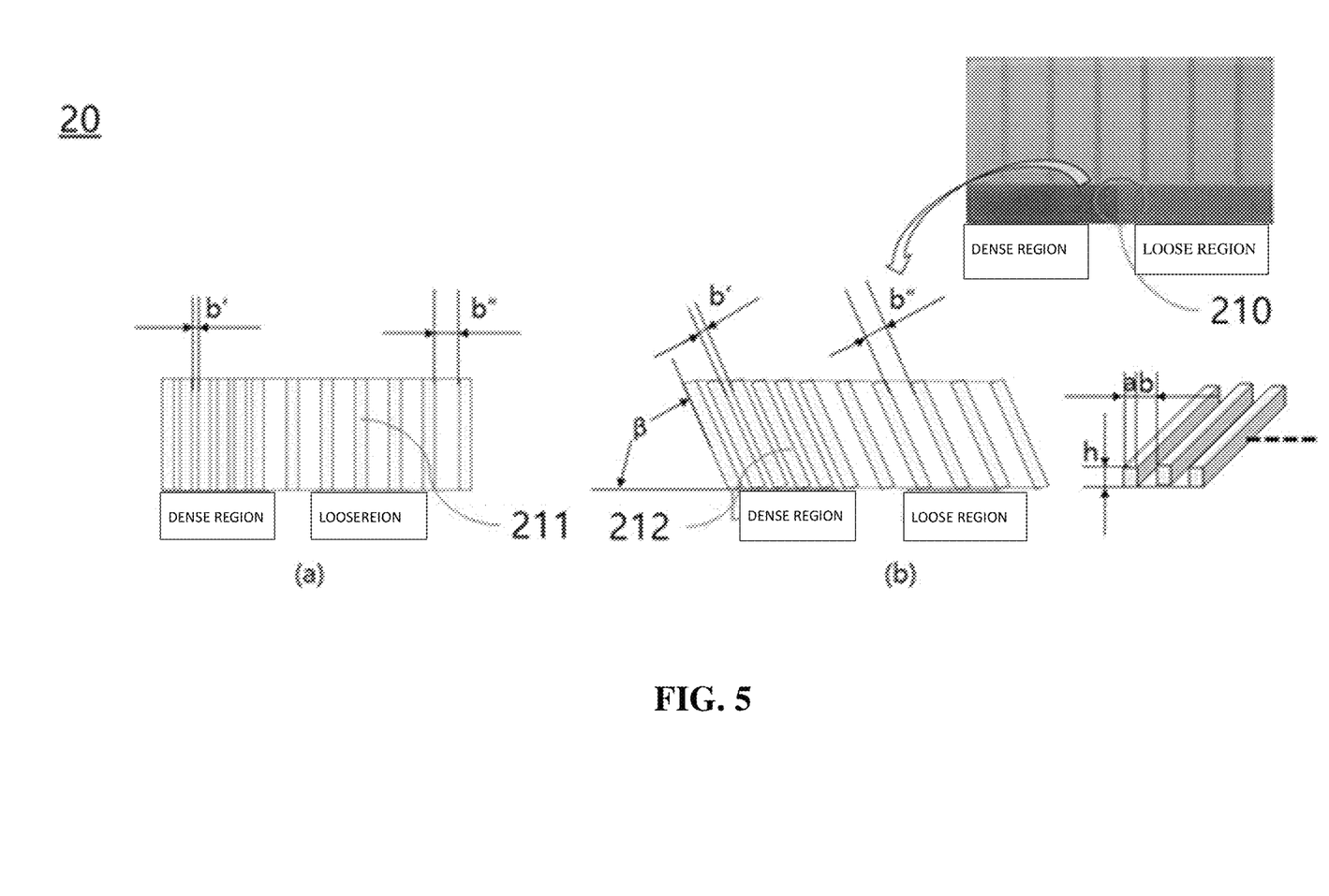
FIG. 5 is a view schematically illustrating stripe protrusions (vertical/inclined) in a dense region and a loose region of a nail polishing part of the foot exfoliator with the high-gloss nail polisher according to the present invention.
Figure 6:
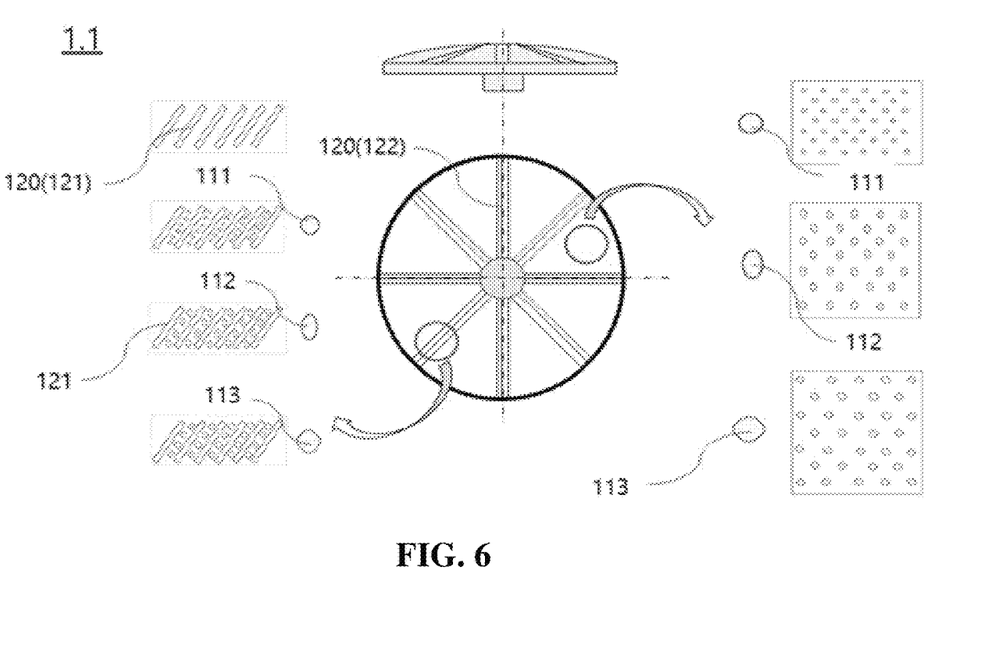
FIG. 6 is a plan view illustrating a configuration of an electric foot exfoliation kit according to another embodiment of the present invention.

FIG. 1 is a picture showing an embodiment of a foot exfoliator with a high-gloss nail polisher according to the present invention. FIG. 2 is a picture showing another embodiment of a foot exfoliator with a high-gloss nail polisher according to the present invention. FIG. 3 shows various embodiments of a protrusion column of a foot exfoliating part of the foot exfoliator with the high-gloss nail polisher according to the present invention, wherein FIG. 3A schematically shows an embodiment in which only comb-pattern stripe protrusions are arranged, FIG. 3B schematically shows an embodiment in which circular protrusions are arranged between the comb-pattern stripe protrusions, FIG. 3C schematically shows an embodiment in which elliptical protrusions are arranged between the comb-pattern stripe protrusions, and FIG. 3D schematically shows an embodiment in which rhombic protrusions are arranged between the comb-pattern stripe protrusions. FIG. 4 shows various embodiments of a protrusion region of the foot exfoliating part of the foot exfoliator with the high-gloss nail polisher according to the present invention, wherein FIG. 4A schematically shows an embodiment in which circular protrusions are arranged, FIG. 4B schematically shows an embodiment in which elliptical protrusions are arranged, and FIG. 4C schematically shows an embodiment in which rhombic protrusions are arranged. FIG. 5 is a view schematically illustrating stripe protrusions (vertical/inclined) in a dense region and a loose region of a nail polishing part of the foot exfoliator with the high-gloss nail polisher according to the present invention. FIG. 6 is a plan view illustrating a configuration of an electric foot exfoliation kit according to another embodiment of the present invention.

Hereinafter, a process of manufacturing the nail polisher and foot exfoliator will be described prior to describing various embodiments of the present invention.

First, chromium (Cr) and metal with excellent chemical resistance are formed on a hard substrate such as a glass substrate, and then a photosensitive film such as a photoresist (PR) film or a dry film photoresist (DFR) film is coated thereon to form a protrusion pattern on the glass. Next, a mask having a protrusion pattern is placed on the PR (or DFR) film to form protruding portions of the nail polisher, and the mask is exposed to ultraviolet (UV) light so that protrusion images are photosensitized on the photosensitive film. Next, the glass substrate irradiated with UV light is immersed in a developer so that the protrusion pattern is formed on the PR (or DFR) film. Then, Cr and glass formed under the PR are sequentially etched so that protrusions are formed on the glass.

Hereinafter, embodiments of a foot exfoliator with a high-gloss nail polisher, which is manufactured using the above manufacturing process, and an electric foot exfoliation kit for the foot exfoliator will be described.

<First Embodiment> Foot Exfoliator with High-Gloss Nail Polisher

Referring to FIGS. 1 and 2, in a foot exfoliator with a high-gloss nail polisher according to the present invention, one surface of a hard plate (not denoted by a reference numeral) such as a glass plate is divided into a foot exfoliating region and a nail polishing region, and a foot exfoliating part 10 and a nail polishing part 20 are configured in respective regions.

In the foot exfoliating part 10 of the foot exfoliator with the high-gloss nail polisher according to the present invention, one protrusion selected from protrusions 110 having a circular shape 111, an elliptical shape 112, and a rhombic shape 113 and a protrusion column 120 are periodically and repeatedly arranged in a predetermined area of the plate.

The protrusion column 120 of the foot exfoliating part 10 of the present invention consists of comb-pattern stripe protrusions 121 or vertical stripe protrusions 122.

The foot exfoliating part 10 to which the comb-pattern stripe protrusions 121 of the protrusion column 120 are coupled will be described in more detail with reference to FIG. 1. A plurality of protrusion 110 regions each formed of one or more protrusions selected from the protrusions 110 having the circular shape 111, the elliptical shape 112, and the rhombic shape 113 (see FIG. 4) and a plurality of protrusion columns 120 consisting of the comb-pattern stripe protrusions 121 formed as if dividing the protrusion 110 regions (see FIG. 3) are arranged on a certain area of the plate.

The comb-pattern stripe protrusions 121 of the protrusion column 120 will be described in more detail with reference to FIG. 3. Between the comb-pattern stripe protrusions 121 which are repeatedly arranged, any one protrusion selected from the protrusions 110 having the circular shape 111, the elliptical shape 112, and the rhombic shape 113 may be further arranged as a plurality of protrusions (see FIGS. 3B, 3C, and 3D). Of course, only the comb-pattern stripe protrusions 121 may constitute the region (see FIG. 3A).

In the foot exfoliating part 10 having the above structure, the circular, elliptical, or rhombic protrusions in the protrusion 110 regions scratch off dead skin cells, and the protrusion columns 120 consisting of the comb-pattern stripe protrusions 121 remove dead skin cells as if cutting off the same and smooth the skin surface.

Also, the circular, elliptical, or rhombic protrusions arranged between the comb-pattern stripe protrusions of the protrusion columns 120 re-polish the dead skin cells raised due to being scratched and thus increase the efficiency of dead skin cell removal.

Here, the protrusions 110 and 121 are formed so that width a of each of the protrusions is in a range of 50 to 1,000 μm, interval b between the protrusions is in a range of 50 to 1,000 μm, and height h of each of the protrusions is in a range of 5 to 1,000 µm, and the comb-pattern stripe protrusions 121 are formed to be inclined at angle of inclination α in a range of 30° to 80°.

The foot exfoliating part 10 to which the vertical stripe protrusions 122 of the protrusion column 120 are coupled will be described in more detail with reference to FIG. 2. A plurality of protrusion 110 regions each formed of one or more protrusions selected from the protrusions 110 having the circular shape 111, the elliptical shape 112, and the rhombic shape 113 (see FIG. 4) and a plurality of protrusion columns 120 consisting of the vertical stripe protrusions 122 formed as if dividing the protrusion 110 regions are arranged on a certain area of the plate.

In the foot exfoliating part 10 having the above structure, the circular, elliptical, or rhombic protrusions in the protrusion 110 regions scratch off dead skin cells, and the protrusion columns 120 consisting of the vertical stripe protrusions 122 remove dead skin cells as if cutting off the same and smooth the skin surface.

Here, the vertical stripe protrusions 122 are formed so that width a of each of the protrusions is in a range of 50 to 1,000 µm, interval b between the protrusions is in a range of 50 to 1,000 µm, and height h of each of the protrusions is in a range of 5 to 1,000 µm.

The nail polishing part 20 of the foot exfoliator with the high-gloss nail polisher according to the present invention is configured by arranging a plurality of vertical stripe protrusions 211, each of which stands upright, or arranging a plurality of inclined stripe protrusions 212, each of which stands obliquely, in order to perform nail polishing in regions of an area of the plate excluding the foot exfoliating part 10.

The nail polishing part 20 of the present invention is divided into a dense region and a loose region, and stripe protrusions 210 may be arranged at different intervals b for each region.

In the nail polishing part 20 having the above structure, the stripe protrusions (vertical/inclined) arranged to be divided into the two different regions are configured to trim a main part of the nail in the loose region and polish the nail and make the nail glossy in the dense region.

Here, the protrusions 210 in the dense region are arranged at intervals b' in a range of 50 to 500 µm, and the protrusions 210 in the loose region are arranged at intervals b" in a range of 500 to 1,000 µm. Also, the inclined stripe protrusions 212 are configured to be inclined at angle of inclination β in a range of 60° to 80°.

<Second Embodiment> Electric Foot Exfoliation Kit for Foot Exfoliator

Referring to FIG. 6, an electric foot exfoliation kit according to the present invention is configured on a round surface of a hard circular plate such as a glass plate so as to be coupled to a foot exfoliator to remove dead skin cells.

The electric foot exfoliation kit according to the present invention is configured on a round surface of a hard circular plate such as a glass plate.

In the electric foot exfoliation kit according to the present invention, one or more protrusions selected from protrusions 110 having a circular shape 111, an elliptical shape 112, and a rhombic shape 113 and protrusion columns 120 are radially arranged from the center.

Also, the protrusion column 120 of the electric foot exfoliation kit according to the present invention consists of comb-pattern stripe protrusions 121 or vertical stripe protrusions 122.

Between the comb-pattern stripe protrusions 121 of the protrusion column 120 of the present invention, any one protrusion selected from the circular, elliptical, and rhombic protrusions is further arranged as a plurality of protrusions.

The foot exfoliator with the high-gloss nail polisher according to the present invention has the following features.

First, one surface of a hard plate such as a glass plate consists of a foot exfoliating region and a nail polishing region.

Therefore, since nail polishing and dead skin cell removal may be simultaneously performed using a single plate, nail and foot care can be performed without causing skin damage.

Also, a foot exfoliating part of the foot exfoliator with the high-gloss nail polisher according to the present invention is configured so that one protrusion selected from circular, elliptical, and rhombic protrusions and protrusion columns (comb-pattern/vertical) disposed at predetermined intervals are periodically and repeatedly arranged.

Therefore, the protrusion selected from the circular, elliptical, and rhombic protrusions scratches off dead skin cells, and the protrusion column removes dead skin cells and smooths the skin surface, and thus it is very effective for dead skin cell removal.

Also, the protrusion column of the foot exfoliating part is configured so that comb-pattern stripe protrusions which are inclined at a predetermined angle are periodically and repeatedly arranged, or any one protrusion selected from the circular, elliptical, and rhombic protrusions is further arranged as a plurality of protrusions between the inclined comb-pattern stripe protrusions.

Therefore, dead skin cells raised due to being scratched are easily removed as if being cut off due to the angle of inclination of the comb-pattern stripe protrusions, and the skin is polished by the circular, elliptical, or rhombic protrusions arranged between the comb-pattern stripe protrusions. Thus, efficiency of dead skin cell removal is very high.

Also, the nail polishing part of the present invention is configured so that it is divided into two regions (dense region/loose region) which are disposed at a predetermined interval, and the stripe protrusions (vertical/inclined) are periodically and repeatedly arranged.

Therefore, by nail trimming being performed in the loose region and polishing being performed in the dense region, there is an advantage of providing a high-gloss nail polisher performing two different tasks using a single product.

In a foot exfoliator with a high-gloss nail polisher according to the present invention, one surface of a hard plate such as a glass plate is divided into a foot exfoliating region and a nail polishing region. Therefore, since nail polishing and dead skin cell removal can be simultaneously performed using a single plate, nail and foot care can be performed without causing skin damage.

A foot exfoliating part of the foot exfoliator with the high-gloss nail polisher according to the present invention is configured so that one protrusion selected from circular, elliptical, and rhombic protrusions and protrusion columns (comb-pattern/vertical) disposed at predetermined intervals are periodically and repeatedly arranged. Therefore, the protrusion selected from the circular, elliptical, and rhombic protrusions scratches off dead skin cells, and the protrusion column removes dead skin cells and smooths the skin surface, and thus it is very effective for dead skin cell removal.

The protrusion column of the foot exfoliating part is configured so that comb-pattern stripe protrusions which are inclined at a predetermined angle are periodically and repeatedly arranged, or any one protrusion selected from the circular, elliptical, and rhombic protrusions is further arranged as a plurality of protrusions between the inclined comb-pattern stripe protrusions. Therefore, dead skin cells raised due to being scratched are easily removed as if being cut off due to the angle of inclination of the comb-pattern stripe protrusions, and the skin is polished by the circular, elliptical, or rhombic protrusions arranged between the comb-pattern stripe protrusions. Thus, efficiency of dead skin cell removal is very high.

The nail polishing part of the present invention is configured so that it is divided into two regions (dense region/loose region) which are disposed at a predetermined interval, and the stripe protrusions (vertical/inclined) are periodically and repeatedly arranged therein. Therefore, by nail trimming being performed in the loose region and polishing being performed in the dense region, there is an advantage of providing a high-gloss nail polisher performing two different tasks using a single product.

The embodiments described herein are only provided to completely inform those of ordinary skill in the art to which the present invention pertains of the scope of the invention. Thus, the embodiments should be understood as illustrative, rather than limiting, in all aspects. The present invention is defined only by the scope of the claims.

What is claimed is:

1. A foot exfoliator with a nail polisher comprising:
   a glass plate;
   a foot exfoliating part disposed on a first region of a surface of the glass plate, having a protrusion region and a protrusion column; and
   a nail polishing part disposed on a second region of the surface of the glass plate,
   wherein the protrusion region has a first plurality of protrusions, each protrusion of the first plurality of protrusions having at least one of a circular shape, an elliptical shape, or a rhombic shape and wherein the protrusion column has a plurality of rectangular prism shaped protrusions and each of the rectangular prism shaped protrusions are inclined at an angle of inclination in a range of 30° to 80°,
   wherein the protrusion region and the protrusion column alternate repeatedly on the first region of the glass plate,
   wherein the protrusion column further comprises a second plurality of protrusions, each protrusion of the second plurality of protrusions having at least one of the circular shape, the elliptical shape, or the rhombic shape,
   wherein the second plurality of protrusions are arranged in a plurality of rows, wherein one row of the plurality of rows is disposed between each of the rectangular prism shaped protrusions of the protrusion column such that the plurality of rows of the second plurality of protrusions alternate repeatedly with the plurality of rectangular prism shaped protrusions,
   wherein a width of each of the rectangular prism shaped protrusions is in a range of 50 to 1,000 μm, an interval between adjacent rectangular prism shaped protrusions is in a range of 50 to 1,000 μm, and a height of each of the rectangular prism shaped protrusions is in a range of 5 to 1,000 μm,
   wherein each of the rectangular prism shaped protrusions continuously extends from one side to an opposite side of the protrusion column along a width of the protrusion column, and wherein the nail polishing part comprises a plurality of inclined stripe protrusions.

2. The foot exfoliator with nail polisher of claim 1, wherein the nail polishing part is divided into a dense region and a loose region, and adjacent inclined stripe protrusions of the dense region are arranged at a different interval from that of adjacent inclined stripe protrusions of the the loose region.

3. The foot exfoliator with nail polisher of claim 2, wherein the adjacent inclined stripe protrusions of the dense region are disposed at an interval of 50 to 500 μm, and the adjacent inclined stripe protrusions of the loose region are disposed at an interval of 500 to 1,000 μm.

4. The foot exfoliator with nail polisher of claim 1, wherein the plurality of inclined stripe protrusions is inclined at an angle of inclination in a range of 60° to 80°.

* * * * *